United States Patent [19]
Morley et al.

[11] Patent Number: 5,766,152
[45] Date of Patent: Jun. 16, 1998

[54] INTRALUMINAL DELIVERY OF TISSUE LYSING MEDIUM

[75] Inventors: Tracey A. Morley, Sunnyvale, Calif.; Paul J. Wang, Chestnut Hill, Mass.

[73] Assignee: Cardima, Inc., Fremont, Calif.

[21] Appl. No.: 695,986

[22] Filed: Aug. 15, 1996

[51] Int. Cl.$^6$ ................................................. A61M 29/00
[52] U.S. Cl. ........................ 604/96; 604/49; 606/194
[58] Field of Search ........................ 604/49, 50, 96, 604/97, 98, 101; 606/192–194; 600/18

[56] References Cited

U.S. PATENT DOCUMENTS

| | | | |
|---|---|---|---|
| 4,689,041 | 8/1987 | Corday et al. | 604/53 |
| 4,850,969 | 7/1989 | Jackson | 604/96 |
| 5,143,093 | 9/1992 | Sahota | 128/898 |
| 5,158,529 | 10/1992 | Kanai | 600/18 |
| 5,279,560 | 1/1994 | Morrill et al. | 604/96 |
| 5,429,605 | 7/1995 | Richling et al. | 604/96 |
| 5,486,192 | 1/1996 | Walinsky et al. | 604/96 X |

OTHER PUBLICATIONS

Angelo A.V. De Paola, MC, et al., Transcoronary Chemical Ablation of Ventricular Tachycardia in Chronic Chagasic Myocarditis, American College of Cardiology, vol. 20:480–482, Aug. 1992.

*Primary Examiner*—John D. Yasko
*Attorney, Agent, or Firm*—Heller Ehrman White & McAuliffe

[57] ABSTRACT

A method and system for lysing a patient's heart tissue causing or involved with arrhythmia which includes an intravascular catheter with a relatively inelastic occlusion balloon on the distal end of the catheter which is inflated to block an artery or vein of the patient's heart so than when lysing fluid such as an ethanol solution is discharged from the distal port in the catheter the inflated balloon prevents the proximal refluxing of lysing medium into undesirable areas of the patient's heart. The inelastic balloon is configured to be inflated to a diameter of about 0.7 to about 1.3, preferably about 0.8 to about 1.2, times the diameter of the blood vessel in which the balloon is to be inflated so as to effectively occlude the passageway without damaging the wall of the blood vessel. The working length of the balloon is less than about 1.5 cm, preferably less than 0.75 cm.

8 Claims, 3 Drawing Sheets

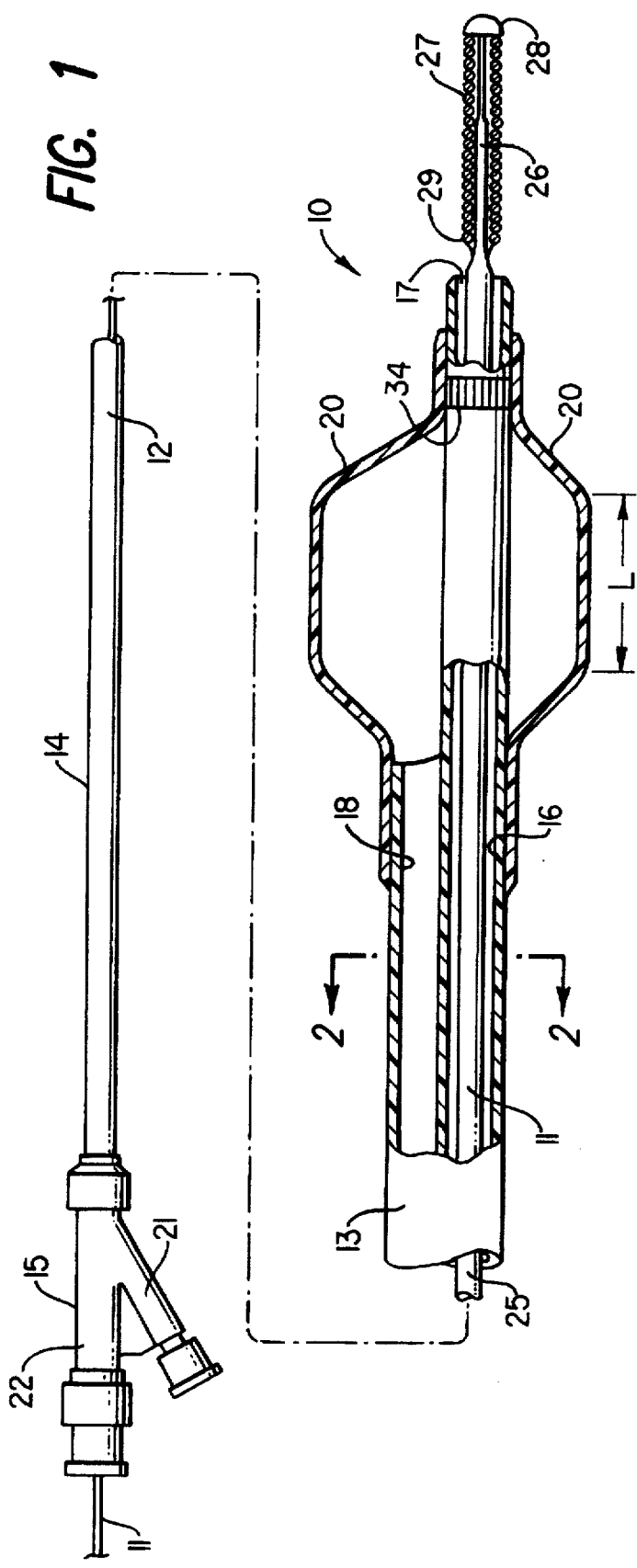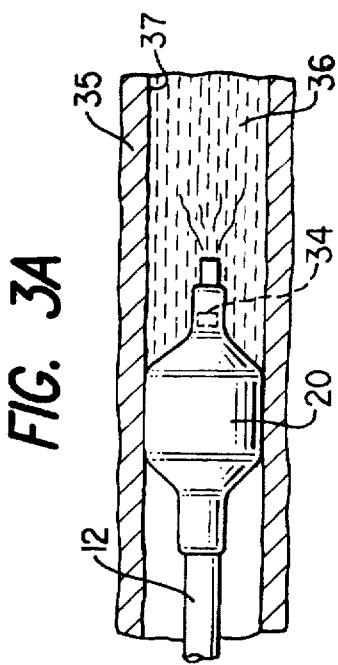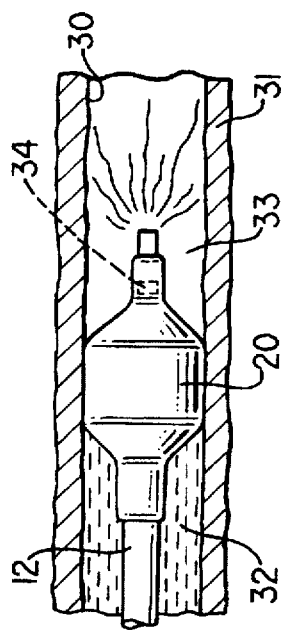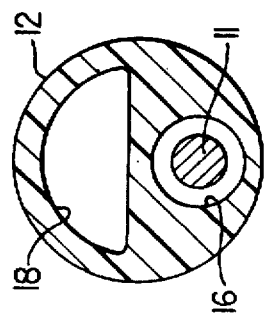

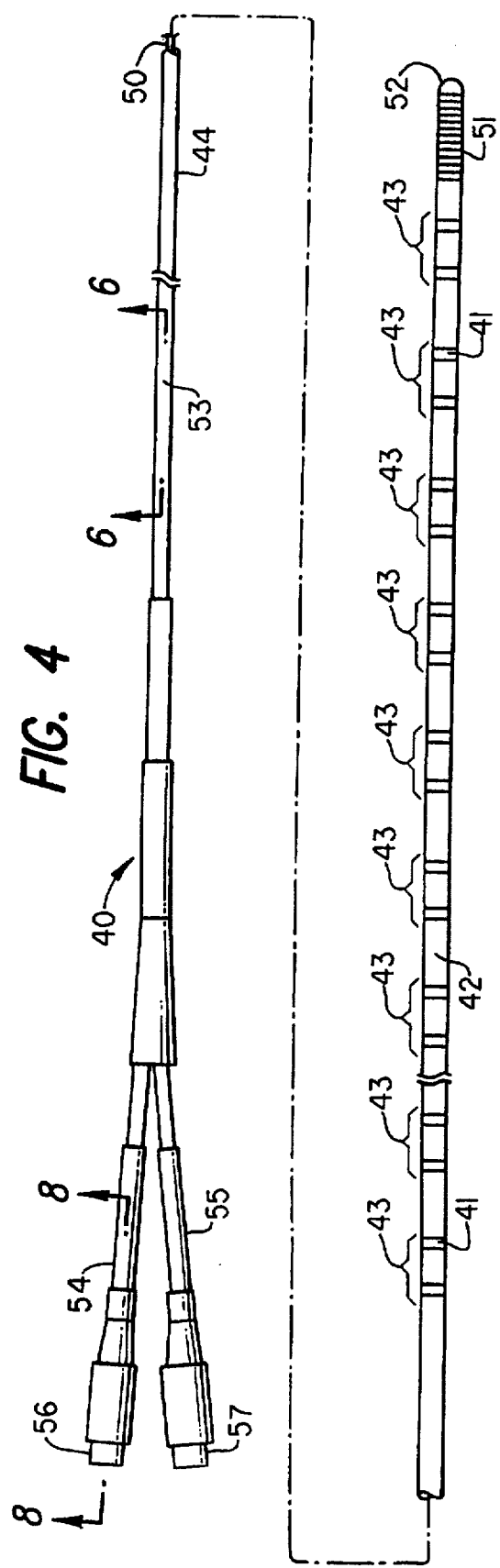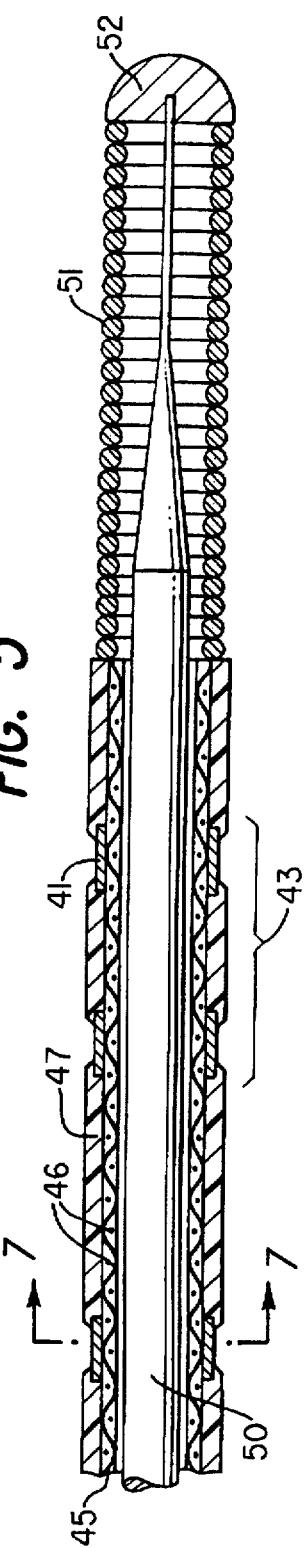

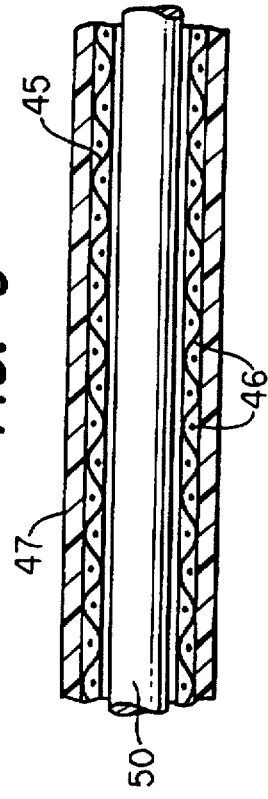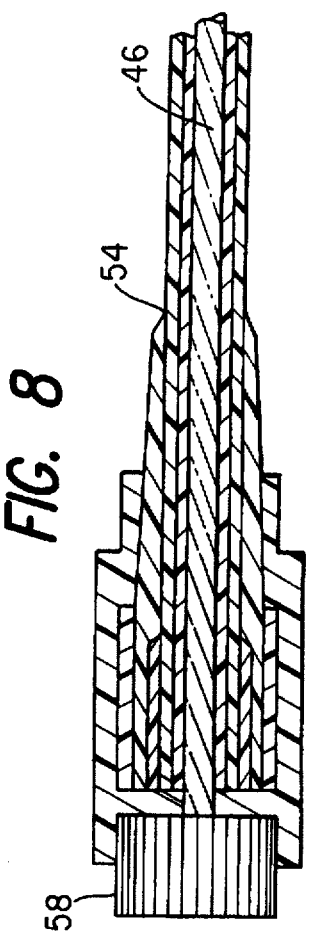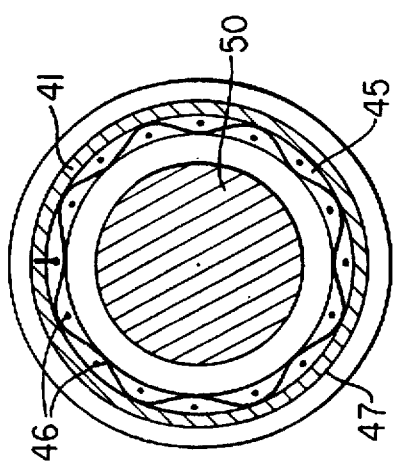

INTRALUMINAL DELIVERY OF TISSUE LYSING MEDIUM

BACKGROUND OF THE INVENTION

This application is directed to the treatment of arrhythmia and particularly to the ablation of ectopic foci causing arrhythmia.

One method which has been used for treating arrhythmic conditions within a patient's heart involves the use of antiarrhythmic drugs such as sodium and calcium channel blockers or drugs which reduce the Beta-adrenergic activity. Another method includes surgically sectioning the origin of the signals causing the arrhythmia or a conducting pathway for such signals. Another frequently used method to terminate an arrhythmia is to destroy the heart tissue at the site from which the signals causing the arrhythmia originate or tissue in a pathway through which such signals pass. The methods used for destroying heart tissue include applying laser, radio frequency (RF) energy or microwave energy to the patient's endocardium at or close to the site from within the patient's left or right ventricle in order to destroy heart tissue involved with the arrhythmia and thereby terminate the irregular heartbeat. The average arrhythmogenic site consists of a projected area of about 1.4 $cm^2$ of endocardial tissue, and a re-entrant site might be much larger. Unfortunately, presently used RF ablation techniques produce lesions about 0.5 $cm^2$ in diameter, so a number of lesions usually must be generated in order to effectively ablate an area of interest sufficiently to terminate the arrhythmia. If the site is not accurately mapped or if there is difficulty in accurately placing and/or holding the distal tip of the ablation device, good tissue surrounding the site which is neither the cause of nor involved with the arrhythmia will be unnecessarily destroyed.

Prior ablation methods typically used elongated intravascular devices with distal portions disposed within a chamber of the patient's heart which have ablating means such as an RF emitting electrode or a laser delivering optical fiber held in contact with the desired region of the patient's endocardium to be destroyed. While this procedure is now widely practiced, precise positioning of the distal ablation portion of the intravascular device at the desired location where the tissue causing or involved with the arrhythmia is to be destroyed remains a formidable problem.

Another method for terminating arrhythmia which has been experimentally used is the chemical ablation of the region of the patient's heart from which the irregular electrical activity originates, such as described by Brugada et al. in "Transcoronary Chemical Ablation of Ventricular Tachycardia", *Circulation* (1989); 79:475–482. In this procedure, iced saline is first directed through a coronary artery which is believed to deliver blood to the ectopic foci or arrhythmogenic site. If the arrhythmia is temporarily terminated by the iced saline indicating that the arterial vessel feeds the origination site, then an aqueous solution of ethanol is delivered through the arterial passageway to lyse the tissue at the origination site and permanently terminate the electrical activity of such tissue. The alcohol solution quickly occludes the arterial passageway at the location into which it is introduced causing a myocardial infarct in the arrhythmogenic region of the patient's heart. Unfortunately, the ethanol solution frequently refluxes to other regions of the patient's heart, making this procedure very difficult to control to a small region of the patient's myocardium. The region of resulting tissue damage can be much larger than necessary to merely terminate the arrhythmia. Due to the extensive risk of extraneous damage to the patient's myocardium from chemical ablation, this procedure has not been used except in limited experimental trials. See also Haines et al. in "Intracoronary Ethanol Ablation In Swine", *J. of Cardiovascular Electrophysiology*, (1994); 5, No. 1, 41–49 and de Paola et al. in "Transcoroanry Chemical Ablation of Ventricular Tachycardia in Chronic Chagasic Myocarditis", *J. of the Ameican College of Cardiology*, (1994); 20, No. 2, 480–482.

What has been needed and heretofore unavailable is a method and system for lysing tissue at a site which causes or is involved with the arrhythmia but which does not destroy an excessive amount of uninvolved tissue. The present invention satisfies these and other needs.

SUMMARY OF THE INVENTION

This invention is directed to a system for the delivery of lysing medium to ablate tissue which either causes arrhythmia or is involved with the conductance of signals which result in arrhythmia.

The system of the invention includes an intravascular catheter which has an elongated shaft with proximal and distal ends, a guidewire port in the distal end, a first inner lumen which extends through at least a portion of the shaft to the port in the distal end of the shaft, a second inner lumen which extends through a portion of the shaft to a location spaced proximally from the distal end of the shaft and an inelastic inflatable member disposed on a distal portion of the shaft. The first inner lumen is configured to slidably receive a guiding member to facilitate the advancement of the intravascular device through the patient's vasculature. The inelastic inflatable member has a nominal working diameter, i.e. in an inflated condition, of at least about 0.7 to not more than about 1.3 times, preferably about 0.8 to about 1.2 times, the diameter of the blood vessel in which the balloon is to be inflated. The balloon has a working length less than about 1.5 cm, and preferably less than about 0.75 cm. As used herein the term inelastic refers to having an elasticity of less than 10% at maximum working pressure. As is recognized by those skilled in the art, blood vessels do not always have circular cross-section, and in those instances, the diameter is an averaged figure based upon the maximum and minimum cross-sectional dimensions.

The inner diameter of the vascular passageway in fluid communication with the tissue to be ablated is first determined to allow the selection and use of an intravascular catheter with an appropriately sized occlusion balloon.

An intravascular catheter of the invention with an appropriately sized balloon is then advanced over an elongated guiding device such as a conventional guidewire to the desired location within the blood vessel, an artery which is believed to direct blood to the tissue at the arrhythmogenic or re-entry site or a vein which is believed to drain blood from such sites. With the occlusion balloon on the catheter in the blood vessel at the location in which the diameter of passageway has been previously determined, the balloon is inflated to a diameter which occludes the passageway of the blood vessel. Tissue lysing media, such as a 96% (by vol.) ethanol solution, is passed through the first inner lumen, out the distal port of the catheter and into the passageway of the blood vessel. The tissue distal to the catheter involved with the arrhythmia is lysed by contact with the ethanol and, additionally, the vascular passageway quickly becomes inflamed when contacted with ethanol, occluding the passageway and preventing the passage of oxygenated blood which thereby ensures that tissue cells are lysed.

The inflated balloon of the catheter blocks the passageway of the blood vessel and prevents any proximal reflux of the ethanol or other lysing fluid into other regions of the patient's heart where such fluid can detrimentally effect good tissue not involved with the arrhythmia. The inflated balloon also prevents the flow of substantial amounts of blood through the passageway which might dilute the ethanol or other lysing fluid and reduce the effectiveness thereof. However, the balloon is sufficiently short to prevent blocking branch arteries leading to regions of the patient's heart which is not involved with the arrhythmia.

In order to ensure that the passageway is in fluid communication with tissue causing or involved with the arrhythmia, iced saline solution is advanced through the second inner lumen of the catheter to discharge the cold fluid into the blood vessel before lysing medium is delivered. The low temperature of the saline solution temporarily paralyzes the heart tissue to which the passageway of the blood vessel leads. If the arrhythmic conditions are terminated by such treatment, then the physician will have reason to believe that the delivery of lysing fluid will contact tissue involved with the arrhythmia and also permanent occlude the arterial passageway and thus will effectively treat the arrhythmia. The balloon on the catheter should be inflated when the iced saline is delivered to prevent proximal reflux of the iced solution which might lead to erroneous indications.

A key requirement for the success of the treatment is to precisely locate the tissue causing or involved with the arrhythmia in order to lyse only a very small region of heart containing such tissue. One presently preferred method of locating the tissue causing or otherwise involved with the arrhythmia is by means of an elongated intravascular device for detecting electrical activity within a patient's heart as described in copending application Ser. No. 08/010,818, filed on Jan. 29, 1993, now abandoned, application Ser. No. 08/043,449, filed Apr. 5, 1993, now abandoned, application Ser. No. 08/057,294, filed May 5, 1993, now abandoned, and application Ser. No. 08/188,619, filed Jan. 27, 1994, now U.S. Pat. No. 5,509,411, which are incorporated herein in their entireties by reference. The devices described in these references have a plurality of sensing electrodes on a distal portion thereof and are advanced within the patient's coronary arteries or cardiac veins so that electrical activity can be detected at various locations within the patient's heart and the sensed electrical activity may then be used to find the intravascular location close to the arrhythmogenic or re-entry site. Once such a site is located, the catheter of the invention can be employed to lyse the tissue at the site. The intravascular device used to detect the electrical activity may also be used to guide the catheter to the site as would a guidewire. When the arrhythmogenic or re-entry site is located, the intravascular device can be left in place, the catheter advanced over the device until the balloon on the catheter is positioned at the desired location where it is inflated and lysing medium delivered to the desire location distal to the occluding balloon on the catheter.

These and other advantages of the invention will become more apparent from the following detailed description thereof when taken in conjunction with the accompanying exemplary drawings.

BRIEF DESCRIPTION OF THE DRAWINGS

FIG. 1 is an elevational view, partially in section, of a catheter assembly embodying features of the invention.

FIG. 2 is a transverse cross-sectional view of the assembly shown in FIG. 1, taken along the lines 2—2.

FIG. 3 is an enlarged view of the distal end of the catheter assembly within a patient's artery with the balloon in an inflated condition to occlude the artery.

FIG. 3A is an enlarged view of the distal end of the catheter assembly within a patient's vein with the balloon in an inflated condition to occlude the vein.

FIG. 4 is an elevational view, partially in section, of a electrophysiology device which may be utilized to detect arrhythmogenic sites.

FIG. 5 is a longitudinal cross-sectional view of the distal portion of the electrophysiology member shown in FIG. 4

FIG. 6 is a longitudinal cross-sectional view of the electrophysiology member shown in FIG. 4 taken along the lines 6—6.

FIG. 7 is a transverse cross-sectional view of the electrophysiology member shown in FIG. 4 taken along the lines 7—7.

FIG. 8 is a longitudinal cross-sectional view of the proximal portion of the electrophysiology member shown in FIG. 4 taken along the lines 8—8.

DETAILED DESCRIPTION OF THE INVENTION

As depicted in FIGS. 1–3, the catheter assembly of a presently preferred embodiment of the invention includes a catheter 10 and a guiding member 11, e.g. a guidewire, over which the catheter is advanced within a patient's vascular system. The catheter 10 has a shaft 12 with a distal portion 13, a proximal portion 14 and an adapter 15 on the proximal end of the catheter shaft. The catheter shaft 12 has a first inner lumen 16 configured to slidably receive the elongated guiding member 11 which extends from the proximal end of the shaft 12 to port 17 in the distal end of the catheter shaft and a second inner lumen 18 which extends from the proximal end to a location proximal to the distal end of the catheter shaft. An inelastic balloon 20, formed of polyethylene terephthalate (PET), polyethylene, polyolefins and the like, is provided on the distal portion 13 which has an interior in fluid communication with the second inner lumen 18. The working length of the balloon 20 is indicated by L.

The adapter 15 on the proximal end of the catheter shaft 12 has a side arm 21 which is in fluid communication with second inner lumen 18 and a central arm 22 which is in fluid communication with the first inner lumen 16.

The guiding member 11 may be a conventional guidewire as depicted in FIGS. 1–3 with a core member 25, a tapered distal section 26 disposed within helical coil 27. The distal end of the coil 27 is secured to the distal end of the tapered distal section 26 by means of solder, brazing, welding and the like to form the rounded plug 28. The proximal end of the coil 27 is secured in a similar manner to the core member 25 at a proximal location 29. The distal portion of the tapered section 26 is typically flatted into a rectangular transverse cross-section to provide increased flexibility in one direction.

In FIG. 3, the catheter 10 is shown disposed within an arterial passageway 30 with the balloon 20 in an inflated condition to its working diameter so as to occlude the passageway. Preferably, the inflated balloon 20 contacts and slightly expands the artery wall 31. A body of blood 32 is disposed within the arterial passageway 30 proximal to the balloon 20 resulting from the occlusion by the inflated balloon and lysing medium 33 is discharged from the distal end of the catheter 10 through port 17 into passageway 30 distal to the balloon. The lysing medium is introduced into the first inner lumen 16 of catheter 10 through the center arm 21 of adapter 15. A suitable lysing medium is a solution of ethanol (e.g. 50% by vol. or greater). Another suitable lysing media which may be used in phenol. As is recognized by those skilled in the art a variety of lysing agents may be employed, either alone or in mixtures thereof. A radiopaque marker 34 is provided on the shaft distal to the balloon 20 to facilitate fluoroscopic determination of balloon location during the procedure.

In FIG. 3A, the blood vessel shown is a cardiac vein 35 with a body 36 of venous blood distal to the inflated balloon 20 within the venous passageway 37. The reference numbers used in this figure are otherwise the same as in FIG. 3

An electrophysiological device 40, as illustrated in FIGS. 4–7, may be used to detect electrical activity causing or involved with the arrhythmia from within the patient's coronary arteries or cardiac veins. This device is described and claimed in copending application Ser. No. 08/188,619, filed on Jan. 27, 1994, and which has been incorporated herein by reference. In this embodiment, the electrophysiological device 40 has a plurality of sensing electrodes 41 disposed on the distal portion 42 in pairs 43 for bipolar mode detection of electrical activity. Details of the distal portion 42 are shown in FIGS. 5 and 7. The shaft 44 is formed of a braided tubular member 45 formed of a plurality of electrical conductors 46. The insulation on separate conductors 46 is exposed under each of the sensing electrodes 41 so that an electrical connection can be made between the electrodes and the electrical conductors. The electrical connection may be secured by means of a suitable solder or brazing material, or by resistance welding, and the electrodes may also be secured to the underlying tubular member by a suitable means such as an adhesive to ensure maintenance of electrical contact with the exposed conductors. All of the strands of the braided tubular member 45 need not be conductors and may be formed of polymer materials such as nylon. A polymer jacket 47 is disposed about the braided tubular member 45 to provide a smoother exterior surface to the device. Suitable polymer materials for the jacket 47 include a high density polyethylene, a thermoplastic polyurethane, polyvinyl chloride, a polyolefinic ionamers such as Surlyn®. Other polymers may also be employed.

A core member 50 is disposed within the inner lumen of the braided tubular member 45 and extends beyond the distal end thereof. A distal coil 51 is disposed about and secured by suitable means, such as brazing, soldering or an appropriate adhesive, to the distal extremity of the core member 50 and is provided with a smooth rounded distal tip 52 formed by joining the distal tip of the coil 51 to the distal extremity of the core member 50. The core 50 may be formed of suitable metallic materials such as stainless steel. Other materials are contemplated.

The proximal section 53 of the device 40 as shown in FIG. 4 has two extensions 54 and 55 which have multi-pin connectors 56 and 57 on the proximal ends thereof. Details of the connector 56 is depicted in FIG. 8. While not shown, each of the electrical conductors 46 are electrically connected to a separate pin 58. A sixteen pin connector is schematically shown in FIG. 8 but connectors having a higher or lower number of pins may be suitable. The electrical conductors 46 are bundled together within the center of the extension.

The electrophysiology device 40 may be used independently of the occluding catheter 10, in which case the device is advanced through the patient's blood vessel to several locations therein to detect electrical activity and from this electrical activity determine the vascular location close to the origination or pathway tissue. The location is noted and the device 40 may then be removed. The device 40 can be advanced through the venous side such as through the patients coronary sinus into the great cardiac vein or other veins which lead to the coronary sinus and the great vein or it can be advanced through the patient's coronary arteries. Once the electrophysiology device is removed, the guidewire 11 and catheter 10 as shown in FIGS. 1 and 2 can be advanced into the veins or arteries of the patient's heart in a conventional manner until the occluding balloon 20 of the catheter 10 is disposed within a blood vessel (artery or vein) at a location in which the inner diameter thereof has been determined and which is in close proximity to and in fluid communication with the tissue involved with the arrhythmia. The occluding balloon 20 may then be inflated to the approximate inner diameter of the blood vessel at the selected location and the lysing medium discharged from the port 17 of the catheter 10 as described above. As previously described, the iced saline may be first discharged to paralyze the tissue distal to the catheter. If the arrhythmia is terminated by the delivery of the iced saline, the physician is reasonably assured that the arrhythmia will be permanently terminated by the delivery of the lysing medium to the same location.

In another method, the electrophysiology device 40 is used as a guidewire where the catheter is slidably mounted onto the device 40 before it is introduced into the patient's vasculature. Both the device 40 and the catheter 10 are then advanced through the vasculature with the distal portion 42 of the device extending out the distal end of the catheter 10 so as to detect electrical activity involved with the arrhythmia. When the arrhythmogenic site or pathway is located, the catheter 10 can then be suitably advanced over the device 40 until the balloon 20 is disposed in a vascular location in fluid communication with the arrhythmogenic or pathway tissue. Inflation of the balloon occludes the vascular passageway 30 and lysing medium can be discharged from the distal port 17 to lyse tissue involve with the arrhythmia. In this instance the electrophysiology device 40 is longer than the catheter 10 and is preferably about 25 to about 75 cm longer than the catheter.

While the present invention is described herein in terms of certain preferred embodiments, those skilled in the art will recognize that various modifications and improvements can be made to the invention without departing from the scope thereof.

What is claimed is:

1. An occluding intravascular catheter for delivery of lysing medium to a blood vessel within a patient's heart having a predetermined inner diameter, comprising:
   a) an elongated shaft having proximal and distal ends, a port in the distal end, a first inner lumen extending within the catheter shaft to the port in the distal end, a second inner lumen extending within the shaft to a location proximal to the distal end; and
   b) an inflatable member on a distal portion of the catheter shaft having an interior in fluid communication with the second inner lumen and having a maximum inflated diameter between about 0.7 to about 1.3 times the predetermined inner diameter of the patient's blood vessel.

2. The intravascular catheter of claim 1 wherein the inflatable member has a working length of less than 1.5 cm.

3. The intravascular catheter of claim 1 wherein the inflatable member has a working length of less than about 0.75 cm.

4. The intravascular catheter of claim 1 wherein the maximum inflated diameter of the inflatable member is about 0.8 to about 1.2 times the inner diameter of the patient's blood vessel.

5. A method for treating a patient's heart exhibiting arrhythmia, comprising:
   a) determining the transverse dimensions of a blood vessel at a desired location within the patient's heart in fluid communication with heart tissue involved with the patient's arrhythmia;
   b) providing a catheter comprising
      a catheter shaft which has proximal and distal ends, a port in the distal end of the catheter, a first inner lumen extending within the catheter shaft to the port in the distal end, a second inner lumen extending within the catheter shaft to a location proximal to the distal end of the catheter shaft,
      an occlusion balloon on a distal portion of the catheter shaft which has a maximum inflated diameter of about 0.7 to about 1.3 times an average transverse inner dimension of the arterial passageway and which has an interior in fluid communication with the second inner lumen;
   e) advancing the catheter within the patient's vasculature until the occluding balloon on the distal portion of the catheter shaft is disposed within the blood vessel at the location in which the inner diameter has been determined;
   f) inflating the occlusion balloon to a diameter of about 0.7 to about 1.3 times the inner dimensions of the blood vessel to occlude the blood vessel; and
   g) directing lysing medium through the first inner lumen of the catheter, out the port in the distal end thereof into the blood vessel to the desired location within the blood vessel distal to the catheter to lyse tissue causing or involved with the arrhythmia, while the balloon occludes the blood vessel to prevent the proximal refluxing of lysing medium to undesirable locations within the patient's heart.

6. The method of claim 5 wherein the balloon is inflated to a diameter of about 0.8 to about 1.2 times an average inner dimension of the blood vessel.

7. A method for treating a patient experiencing arrhythmia, comprising:
   a) advancing at least one intravascular guidewire having a plurality of sensing electrodes on a distal portion thereof through the patient's coronary arterial system;
   b) detecting electrical activity from heart tissue to locate heart tissue causing or involved with the arrhythmia;
   c) determining an average inner dimension of a coronary artery which is in fluid communication with heart tissue causing or involved with the arrhythmia;
   d) providing a catheter comprising
      a catheter shaft which has proximal and distal ends, a port in the distal end of the catheter, a first inner lumen extending within the catheter shaft to the port in the distal end, a second inner lumen extending within the catheter shaft to a location proximal to the distal end of the catheter shaft,
      a relatively short occlusion balloon on a distal portion of the catheter shaft which has a maximum inflated diameter of between about 0.7 to about 1.3 of the determined inner diameter of the coronary artery and which has an interior in fluid communication with the second inner lumen;
   e) advancing the catheter over the guidewire with the guidewire slidably disposed within the first inner lumen until the balloon on the distal portion of the catheter shaft is located at a desired location within the patient's coronary artery;
   f) passing inflation fluid through the second inner lumen into the interior of the balloon to inflate the balloon until the diameter of the inflated balloon is about 0.7 to about 1.3 times the determined inner diameter of the coronary artery at a desired location so as to occlude the arterial passageway thereof sufficiently to prevent the proximal passage of significant quantities of lysing medium by the inflated balloon; and
   g) directing lysing medium through the first inner lumen of the catheter and out the port in the distal end thereof while the balloon is inflated to deliver said lysing medium to the desired location within the coronary artery distal to the catheter to lyse tissue causing or involved with arrhythmia.

8. The method of claim 7 wherein the balloon is inflated to a diameter of about 0.9 to about 1.1 times the determined diameter of the coronary artery.

* * * * *